March 16, 1976 J. C. MIKKELSEN Plant Pat. 3,841
BEGONIA PLANT
Filed Feb. 28, 1974
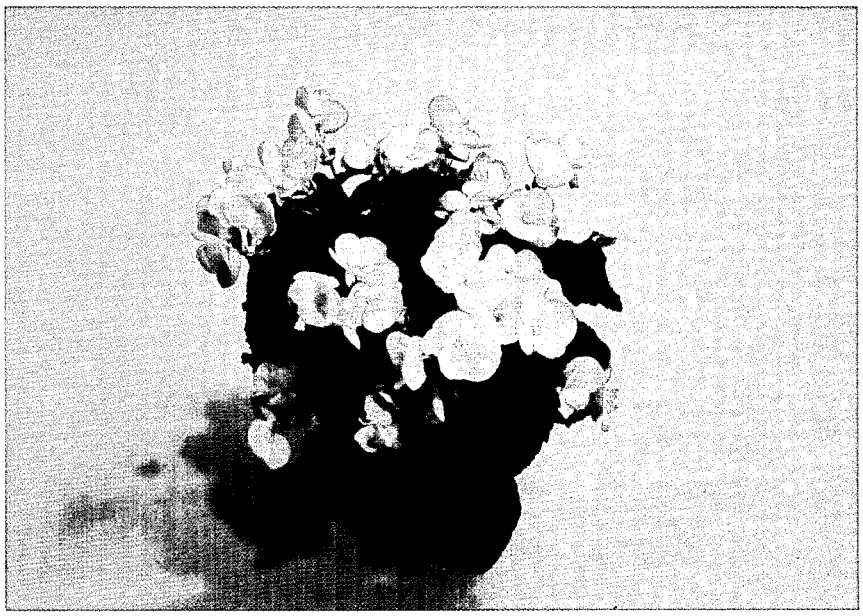

United States Patent

Plant Pat. 3,841
Patented Mar. 16, 1976

3,841
BEGONIA PLANT

James C. Mikkelsen, Ashtabula, Ohio, assignor to Mikkelsens, Inc., Ashtabula, Ohio Filed Feb. 28, 1974, Ser. No. 446,785
Int. Cl. A01h 5/00
U.S. Cl. Plt.—68 1 Claim The present invention relates to a new and distinctive cultivar of begonia plant known by the varietal name Schwabenland Gold and botanically known as *Begonia elatior*. The new variety was discovered by me in a greenhouse in Ashtabula, Ohio, as a single shoot mutation on a multi-shooted plant of the variety Krefeld Orange, disclosed in U.S. Plant Pat. 3,403, issued Sept. 18, 1973, in the name of Siegfried Merholz. Asexual reproduction by stem and leaf cuttings has reproduced the unique features of the new variety through successive propagations.

The following characteristics distinguish the new begonia from both its parent and other begonias commercially known and used in the floriculture industry:

1. Semi-dwarf growth characteristics.
2. Close internodes producing compact plant.
3. Smaller flowers than the parent Krefeld Orange or sub parent, namely, the variety Schwabenland, disclosed in U.S. Plant Pat. 3,320, granted Mar. 13, 1973.
4. A new distinct deep golden orange color not previously available in this series of begonias.
5. Extremely easy to root.
6. Produces a profusion of adventitious shoots at the base of leaf petioles when propagated by leaf cuttings.
7. Foliage is green compared to the red pigmented coloring of foliage and stems of parent variety.
8. Short compact growth results in potential use of the new variety in outdoor gardens. The new cultivar when fully grown is approximately 8"–10" in height and 8"–10" in diameter.

The accompanying colored photographic drawing illustrates the overall appearance of this variety taken as a face view of the plant and showing the colors as true as it is reasonably possible to obtain in a colored reproduction of this type.

The following is a detailed description of my new begonia variety based on plants produced under commercial practices in the green houses of Mikkelsens Inc., Ashtabula, Ohio. Color references are made to the Royal Horticultural Society Colour Chart except where general color terms of ordinary dictionary significance are used.

Parentage: Mutation of Krefeld Orange.

Propagation: By leaf cuttings, with propagation being approximately 1–2 weeks faster (7–8 weeks) in high light periods and approximately 2 weeks faster (12 weeks) in low light periods, under similar growing conditions, when compared to the other Schwabenland *elatior* begonias; initiation of adventitious buds is substantially greater (30%) compared to parent variety.

Rooting habit: Rapid, fibrous, fine roots.

Form: Plant is bushy, being full with an abundance of adventitious shoots.

Habit of growth: Upright with average vigor; if given sufficient space to avoid stretching the new variety is adequately self-supporting.

Blooming habits: Individual flowers are borne on a sturdy pedicel branching from a firm peduncle of the total cyme.

Blooming season: Normal season is mid-November in latitudes equal to Ashtabula, Ohio.

Foliage: Well textured, film glabrous, alternating, having the leaf petiole at a narrow angle to the stem.

*Size.*—Cordate, crenate.

*Margin.*—Quite wavy between sinus.

*Color.*—Old top, between 147A–B. Under, near 138B. New top, near 137C. Under, near 148B.

Disease resistance: Apparently more resistent to common mildew than other *elatior* begonias of this type when grown under the same environment.

Flowers:

*Borne.*—On sturdy cymes, with the flowers being considerably smaller than the other cultivars of the Schwabenland types; flowering continues for periods of several months, having best color rendition under good light conditions, 5–7 cm. diameter.

*Quantity.*—Very floriferous, making up in quantity of blooms that quality lost in size. Individual blooms last approximately 2–4 weeks.

*Buds.*—Flat, showing reverse coloring of tepals 44–D.

*Tepals.*—Flat, color orange-red 30A–B, as compared with the more reddish orange-red color of Krefeld Orange, 40–A.

*Reproductive organs.*—Stamens—Yellow—12A–B, abundant, long lasting. Pollen—Abundant, light yellow 11–B. Styles/ovaries—None seen to date.

I claim:

1. A new and distinct cultivar of *elatior* begonia characterized particularly by its distinctive deep golden orange flower color; semi-dwarf and short compact growth characteristics; close internodes which produce a compact plant; relatively small flowers, approximately 5–7 cm. in diameter; easy rooting characteristics; production of a profusion of adventitious shoots at the base of leaf petioles when propagated by leaf cuttings, and by its more floriferous habit than other Schwabenland type begonias.

No references cited.

ROBERT E. BAGWILL, Examiner